United States Patent [19]
Lin et al.

[11] Patent Number: 5,957,138
[45] Date of Patent: *Sep. 28, 1999

[54] METHOD AND APPARATUS FOR THREE-DIMENSIONAL FLOW LUMEN IMAGING

[75] Inventors: Gregory Sharat Lin, Fremont; Ray Steven Spratt, San Jose; Dennis Paul, Mountain View, all of Calif.

[73] Assignee: Diasonics Ultrasound, Inc., Milpitas, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/918,250

[22] Filed: Aug. 25, 1997

[51] Int. Cl.$^6$ ........................................................ A61B 8/00
[52] U.S. Cl. ............................................ 128/916; 600/453
[58] Field of Search ............................. 128/916; 600/441, 600/442, 443

[56] References Cited

U.S. PATENT DOCUMENTS

| | | |
|---|---|---|
| 5,127,409 | 7/1992 | Daigle . |
| 5,282,471 | 2/1994 | Sato . |
| 5,295,486 | 3/1994 | Wollschlager et al. . |
| 5,315,512 | 5/1994 | Roth ......................................... 600/442 |
| 5,329,929 | 7/1994 | Sato et al. ............................... 128/916 |
| 5,394,874 | 3/1995 | Forestieri et al. . |
| 5,446,800 | 8/1995 | Briggs et al. . |
| 5,454,371 | 10/1995 | Fenster et al. . |
| 5,474,073 | 12/1995 | Schwartz et al. . |
| 5,485,842 | 1/1996 | Quistgaard . |
| 5,520,185 | 5/1996 | Soni et al. ............................... 128/916 |
| 5,615,679 | 4/1997 | Ri et al. ................................... 600/441 |

OTHER PUBLICATIONS

Nelson, T. R. and Elyins, T. T., Visualization of 3D Ultrasound Data, IEEE Computer Graphics and Applications (1993), vol. 13, No. 6, pp. 50–57.

Selzer, R. H., Lee, P. L., Lai, et al., Computer–Generated 3D Ultrasound Images of the Carotid Artery, IEEE Computer Society (1988), pp. 21–26.

Wells, P. N. T., Ultrasonic Colour Flow Imaging, Physics in Medicine & Biology, (1994), vol. 39, No. 12, pp. 2113–2145.

Coleman, D. J., Woods, S., Rondeau, M. J., and Silverman, R. H., Ophthalmic Ultrasonography, Radiologic Clinics of North America (1992), vol. 30, No. 5, pp. 1105–1114.

Miyagi, Y., Masaoka, H., Akamatsu, N. and Sekiba, K., Development of a three–dimensional color Doppler system, Medical Progress through Technology (1993), vol. 18, No. 4, pgs.

Carson, P.L., Li, X., et al., Approximate Quantification of Detected Fractional Blood Volume in the Breast by 3D Color Flow and Doppler Signal Amplitute Imaging, Ultrasonics Symposium Proceedings, IEEE (1993), pp. 1023–1026.

Ohbuchi, R. and Fuchs, H., Incremental 3D Ultrasound Imaging from a 2D scanner, Proceedings of the First Conference on Visualization in Biomedical Computing, IEEE (1990), pp. 360–367.

Greenleaf, J. F., Three–Dimensional Imaging in Ultrasound, Journal of Medical Systems (1982), vol. 6, No. 6, pp. 579–589.

(List continued on next page.)

*Primary Examiner*—Marvin M. Lateef
*Assistant Examiner*—Ali M. Imam
*Attorney, Agent, or Firm*—Blakely, Sokoloff, Taylor & Zafman LLP

[57] ABSTRACT

A method and apparatus for generating three-dimensional (3D) images of flow structures and their flow lumen using ultrasound techniques. According to one aspect of the invention, a border between a flow region and a non-flow region is used to render a three-dimensional image of the flow lumen of the flow structure. The images may be viewed in real-time and/or stored on a machine-readable medium. In one embodiment, the three-dimensional images may be manipulated in a number of viewing directions/angles/distances/positions/styles. In one embodiment, a flow lumen may be displayed using a virtual angioscopic view.

24 Claims, 7 Drawing Sheets

OTHER PUBLICATIONS

Fishman, E. K., Magid, D., et al., Three-dimensional Imaging, Radiology (1991), vol. 181, No. 2, pp. 321–337.

Cavaye, D. M., Tabbara, M. R., Three Dimensional Vascular Ultrasound Imaging, The American Surgeon (1991), vol. 57, No. 12, pp. 751–755.

Cavaye, D. M., White, R. A., et al., Three-dimensional intravascular ultrasound imaging of normal and diseased canine and human arteries, Journal of Vascular Surgery (1992), vol. 16, No. 4, pp. 509–519.

Crass, J. R., Miller, C., et al., Radiological Application of Three-Dimensional Imaging Systems, Seminars in Ultrasound CT and MRI (1992), vol. 13, No. 2, pp. 94–101.

Rubin, J. M., Bude, R. O., Power Doppler US: A Potentially Useful Alternative to Mean Frequency–based Color Doppler US, Radiology (1994), vol. 190, No. 3, pp. 853–856.

Bude, R. O., Rubin, J. M., Power versus Conventional Color Doppler Sonography: Comparison in the Depiction of Normal Intrarenal Vasculature, Radiology (1994), vol. 192, No. 3, pp. 777–780.

Picot, P. A., Rickey, D. W., et al., Three–Dimensional Colour Doppler Imaging, Ultrasound in Medicine and Biology (1993), vol. 19, No. 2, pp. 95–104.

Downey, D. B. and Fenster, A., Vascular Imaging with a Three–Dimensional Power Doppler System, American Journal of Roentgenology (1995), vol. 165, No. 3, pp. 665–668.

Ritchie, C. J., Edwards, W. S., et al., Three Dimensional Ultrasonic Angiography Using Power–Mode Doppler, Ultrasound in Medicine and Biology (1996), vol. 22, No. 3, pp. 277–286.

Guo, Z. and Fenster, A., Three–Dimensional Power Doppler Imaging: A Phantom Study to Quantify Vessel Stenosis, Ultrasound in Medicine and Biology (1996), vol. 22, No. 8, pp. 1059–1069.

Pretorius, D. H., Nelson, T. R., et al., 3–Dimensional Sonographic Analysis Based on Color Flow Doppler and Gray Scale Image Data: A Preliminary Report, Journal of Ultrasound in Medicine, (1992), vol. 11, No. 5, pp. 225–232.

Tamura, S., et al., Three–Dimensional Reconstruction of Echocardiograms Based on Orthogonal Sections, Pattern Recognition (1985), vol. 13, No. 2, pp. 115–124.

McCann, Hugh A., et al., Multidemensional Ultrasonic Imaging for Cardiology Proceedings of the IEEE (1988), vol. 76, No. 9, pp. 1063–1073.

METHOD AND APPARATUS FOR THREE-DIMENSIONAL FLOW LUMEN IMAGING

BACKGROUND OF THE INVENTION

1. Field of the Invention

The invention relates to the field of ultrasound imaging. More specifically, the invention relates to three-dimensional imaging of flow structures using ultrasound imaging techniques.

2. Background Information

Various techniques and systems may be used to obtain images of the interior of a body and/or flow structures within a body. (A body is used herein to refer to various types of subjects, such humans, animals, non-living structures, etc., while flow structure as used herein may refer to a region of fluid flow such as occurring in veins, arteries, etc.)

To detect and display flow structures in three-dimensional views, several data acquisition and imaging techniques may be utilized, such as magnetic resonance imaging (MRI), CT, and ultrasound. In some applications, it is particularly useful to view the flow lumen, which usually, but not always, corresponds to the "hollow" interior cavity of a flow structure in a body. For example, imaging of flow lumen may be desired to view irregular regions that may be present in the interior of the flow structure, e.g., intimal defects, plaque, stenosis, etc., which may occur on the interior wall of an artery, vein, or other vessel. To view the flow lumen, MRI, CT, and contrast X-ray angiography imaging techniques have typically been used. However, the ionizing radiation of X-ray and CT and the substantial expense and inconvenience associated with MRI and CT equipment may often limit the use of such systems.

Ultrasound imaging techniques, on the other hand, typically provide substantially greater convenience and cost efficiency, to both the equipment operator and the subject (body), compared to the X-ray, MRI and CT imaging techniques. Ultrasound techniques that facilitate three-dimensional imaging of flow structures within a body generally involve the following steps: (1) detecting a flow structure using Doppler signals, wherein a predetermined power/amplitude/magnitude and/or frequency/velocity Doppler threshold is used to distinguish a flow region (e.g., a flow structure) from a non-flow region; (2) collecting power and/or frequency Doppler data at a number of sample volumes and/or planes (or "slices") of the flow structure; and (3) consolidating the data for the various sample volumes and/or slices of the flow structure to generate a three-dimensional, solid image of the flow structure (i.e., an image having the interior of the flow structure completely filled up; free from cavities, such that the flow lumen is not depicted from the inside of the flow structure).

However, ultrasound techniques generally do not provide the quality and accuracy of images as obtained from relatively more complex/expensive imaging techniques, such as X-ray, MRI and CT. Furthermore, previous ultrasound imaging techniques were typically limited to generating solid 3D images of flow structures. Unfortunately, solid 3D images of flow structures, as produced by past ultrasound techniques, have been unable to depict desired images of the flow lumen, such as, for example, the interior wall, including irregularities, of an artery, vein, or other vessel.

SUMMARY OF THE INVENTION

The present invention provides a method and apparatus for three-dimensional (3D) images of flow structures using ultrasound techniques. Using ultrasound techniques, a flow structure is detected. The flow structure may or may not include the physical "wall" defining the flow structure (e.g., the physical wall of an artery) and/or areas of non-flow that may occur within/upon the physical wall of the flow structure.

By detecting the edge of the flow structure, which in many instances approximates the physical wall (or edge) enclosing the detected flow (e.g., the physical wall of an artery), the present invention provides a three-dimensional view of the interior region(s) of the flow structure (i.e., the flow lumen). According to one embodiment of the invention, the 3D image of the flow lumen may approximate the physical structure enclosing a flow structure, such as, for example, the interior wall(s) of an artery, vein, or other vessel.

According one aspect of the invention, a three-dimensional image of the flow lumen may be interactively-controllable to provide several types of views of a flow structure and the interior of the flow structure itself, including a "virtual" angioscopic view. When a virtual angioscopic viewing mode is used, an end-to-end tubular or "tunnel" view of the flow lumen that allows "looking through" and/or "moving through" the flow lumen is provided, which may simulate images provided by an angioscope. Thus, the interior of the flow structure, including any irregularities may be viewed (e.g., intimal defects, plaque, stenosis, stents, etc., which may be present in the interior wall of an artery, vein, or other vessel).

DETAILED DESCRIPTION

In the following description, numerous specific details are set forth to provide a thorough understanding of the invention. However, it is understood that the invention may be practiced without these specific details. In other instances, well-known circuits, structures and techniques have not been shown in detail in order not to obscure the invention.

DESCRIPTION OF AN EMBODIMENT OF THE INVENTION

Figure 1:
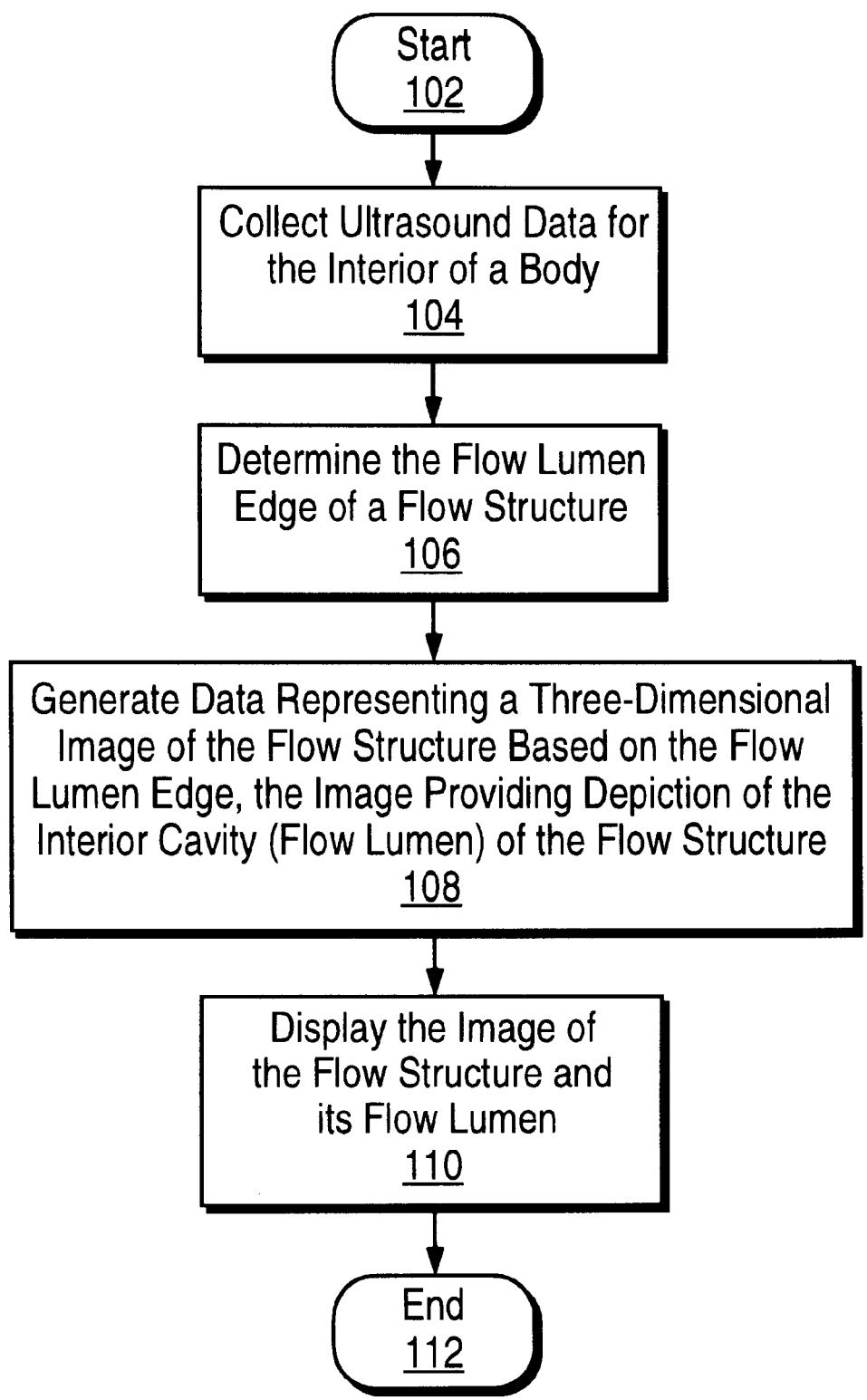
FIG. 1 is a flow diagram illustrating a method for providing 3D ultrasonic flow lumen images according to one embodiment of the invention.

FIG. 1A is a flow diagram illustrating a method for providing 3D ultrasonic flow lumen images according to one embodiment of the invention. Flow begins at step 102 and ends at step 112. From step 102, flow passes to step 104.

In step 104, ultrasound data is collected for one or more samples in a body, and flow passes to step 106. The samples may be planar (e.g., two-dimensional (2D) planes/slices) and/or volumetric regions of the interior of a body. In one embodiment, power (also referred to amplitude or magnitude) Doppler and/or frequency shift (also referred to as velocity or color) Doppler data is obtained by transmitting ultrasound signals into the body, receiving from the body signals (or echoes) that are based on the transmitted signals, and processing the received signals using Doppler data processing techniques and/or circuitry. Utilizing a predetermined and/or adaptive Doppler power and/or frequency shift threshold, areas of flow, and correspondingly, flow structures can be determined in the body. In alternative embodiments, techniques other than power and/or frequency Doppler may be utilized to collect and/or process data from the interior of the body, and to determine regions of flow (or flow structures).

In step 106, the flow lumen edge of the flow structure is determined, and flow passes to step 108. Techniques for determining the flow lumen edge of the flow structure according to several embodiments of the invention are described in further detail below with reference to FIGS. 2A–2C.

In step 108, data representing a 3D image of the flow structure is generated based on the lumen edge determined in step 106, and flow passes to step 110. Exemplary 3D images of flow structures that may be generated according to several embodiments of the present invention are below with reference to FIGS. 4A–4B.

In one embodiment, the data representing the 3D image of the flow lumen is generated by repeating steps 104 and 106 for a number of substantially parallel 2D slices/planes to "build up" a volumetric 3D image of the flow structure, and in particular, its flow lumen, as described with reference to FIG. 3A–3C. The repetition of steps 104 and 106 for the plurality of 2D planes could be performed mechanically (e.g., by translating an ultrasound probe perpendicular to the 2D planes/slices of the flow structure) and/or electronically. Furthermore, for each 2D plane for which ultrasound data is obtained, data representing the entire flow structure, the flow lumen edge, and/or non-flow regions may be stored. For example, in one embodiment, only data for the flow lumen edge is stored for each 2D plane. In an alternative embodiment, all of the data for the flow structure region and the nonflow structure region (e.g., the flow lumen edge and the flow lumen interior) is stored.

It should be appreciated that while one embodiment is described wherein flow lumen edge determination (step 106) is performed prior to generating a 3D image (step 108), in alternative embodiments, flow lumen edge determination may be performed subsequent to generating the data representing a 3D image of the flow structure. Furthermore, in alternative embodiments, a 3D image of a flow structure and its flow lumen may be generated without using substantially parallel 2D planes. For example, in one embodiment, data representing a volumetric 3D image may be generated using a number of 2D planes that intersect or meet at an axis, as described with reference to FIGS. 3B–3C.

In step 110, the 3D image is displayed to provide views of the flow structure, and in particular, its flow lumen, and flow passes to step 112, where flow ends. In one embodiment, the 3D image represented by the data generated in step 108 can be interactively controllable to provide fully rotatable and positionable views of an interior portion (i.e., the regions(s) defining the flow lumen) of the flow structure (e.g., a virtual angioscopic view).

Figure 2A:
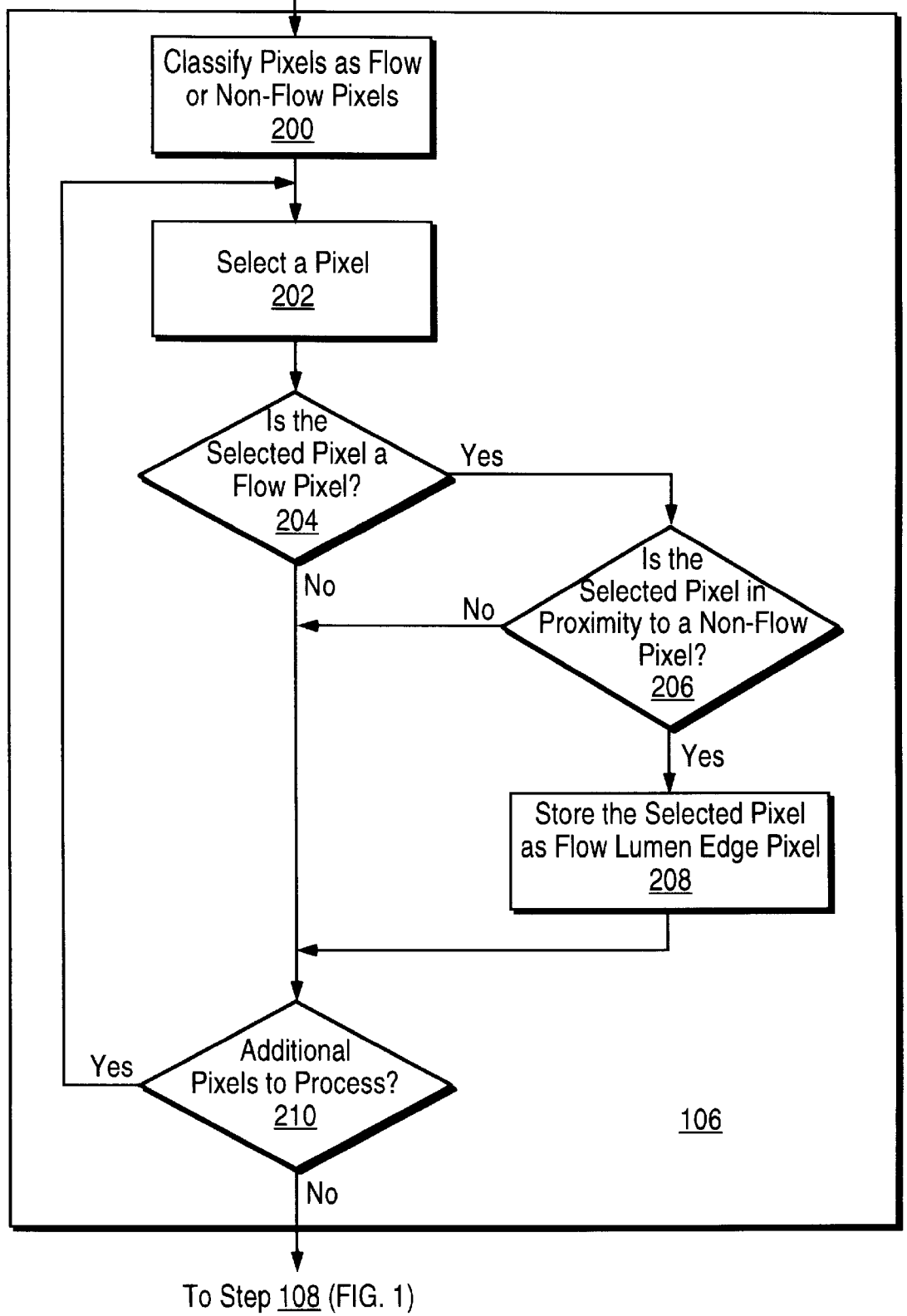
FIG. 2A is a flow diagram illustrating a method for determining the flow lumen edge of a flow structure according to one embodiment of the invention.

FIG. 2A is a flow diagram illustrating a method for determining the flow lumen edge of a flow structure according to one embodiment of the invention. To aid in the understanding of the flow lumen edge determination according to the described embodiment, FIG. 2A will be described in conjunction with FIGS. 2B and 2C, which illustrate determination of the flow lumen edge according to an embodiment of the invention.

In FIG. 2A, flow passes from step 104 to step 200. In step 200, each pixel is encoded as a flow pixel or a non-flow pixel. In the described embodiment, Doppler techniques (e.g., power and/or frequency Doppler), and in particular, a power and/or frequency Doppler threshold is utilized to determine a region of flow in a body, and hence a flow structure. For example, in an embodiment wherein power Doppler is used, a threshold Doppler signal amplitude may be used to determine a flow region and/or a non-flow region (e.g., regions that exceed the power Doppler signal amplitude will be considered as flow regions, while other regions may be considered as non-flow regions).

Once detected using ultrasound techniques (e.g., Doppler), the flow region or the non-flow region may be digitally encoded in one embodiment of the invention. For example, a binary value (e.g., one or more bits) could be used to encode pixels as flow pixels (i.e., pixels belonging to a flow region according to the power and/or frequency Doppler threshold) or non-flow pixels (i.e., pixels belonging to non-flow regions according to the power and/or frequency Doppler threshold).

In step 202, a pixel is selected, and flow passes to step 204.

In step 204, if it is determined that the selected pixel is a "flow pixel" corresponding to a region of flow (i.e., a flow structure), flow passes to step 206. Otherwise, flow passes to step 210.

Figure 2B:
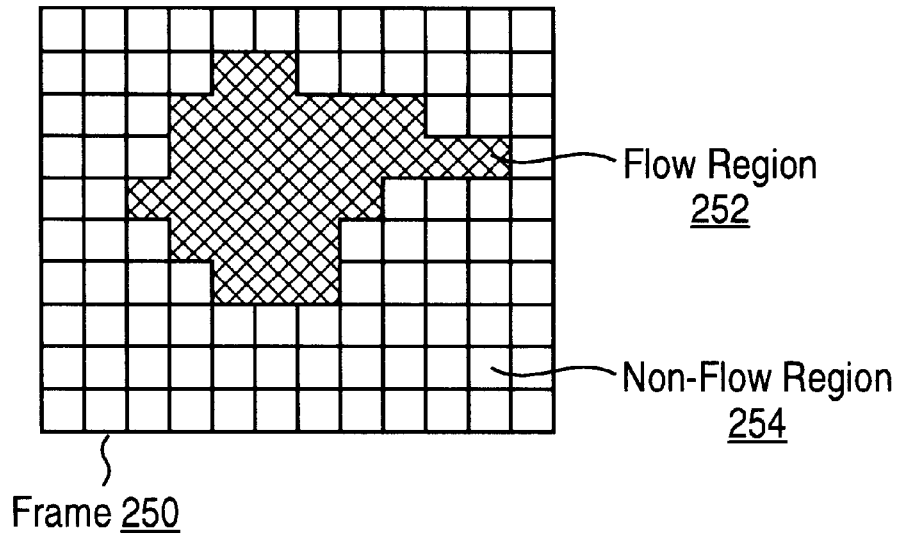
FIGS. 2B is a diagram illustrating determination of the flow lumen edge and interior of a flow structure according to one embodiment of the invention.

Now referring to FIG. 2B, a frame 250, which represents a sample (two-dimensional) plane of image data, which may be represented by pixels, is shown. The frame 250 includes a flow region 252 comprising flow pixels and a non-flow region 254 comprising non-flow pixels. Accordingly, the flow region 252 represents a flow structure (i.e., a region where flow is detected according to a threshold, such as a Doppler power threshold) while the non-flow region 254 represents a region in the body where flow is not detected.

As mentioned above, the determination of flow regions (or structures) and non-flow regions may be performed according to several methods in alternative embodiments of the invention. For example, in one embodiment, power Doppler and/or frequency shift Doppler ultrasound techniques that make such a determination based on power, frequency, and/or other thresholds may be used to detect flow regions (or structures) and/or non-flow regions. As depicted in FIG. 2B, the flow region 252 is shown, for illustrative purposes, with dark shading, while the non-flow region 254 is depicted without shading.

Referring back to FIG. 2A, at step 206, it is determined whether the selected flow pixel is a flow lumen edge pixel. In the described embodiment, the determination of flow lumen edge pixels (i.e., pixels that substantially define a border/edge of a flow region) is done at step 206 by determining whether the selected flow pixel is in proximity, within a predetermined threshold, to a non-flow pixel. If the selected flow pixel is in proximity to a non-flow pixel, then flow passes to step 208, wherein the selected pixel is stored as a flow lumen edge pixel. Otherwise, flow passes to step 210.

In one embodiment, any flow pixel that is adjacent to at least one non-flow pixel is considered to be a flow lumen edge pixel. Accordingly, in FIG. 2C, the frame 250 is shown having a flow lumen edge region 256 which includes pixels of the flow region 252 shown in FIG. 2B that are adjacent to at least one pixel in the non-flow region 254. Thus, the flow lumen edge region 256 is comprised of flow pixels in the flow region 252 of FIG. 2B that are not completely surrounded (e.g., above, below, left, and to the right) by other flow pixels.

From steps 204 and 208, flow passes to step 210. In step 210, if additional pixels require processing (e.g., for the current frame or 2D slice, such as the frame 250), flow passes back to step 202, wherein another pixel is selected. Otherwise, flow passes to step 108 of the flow diagram illustrated in FIG. 1.

Figure 2C:
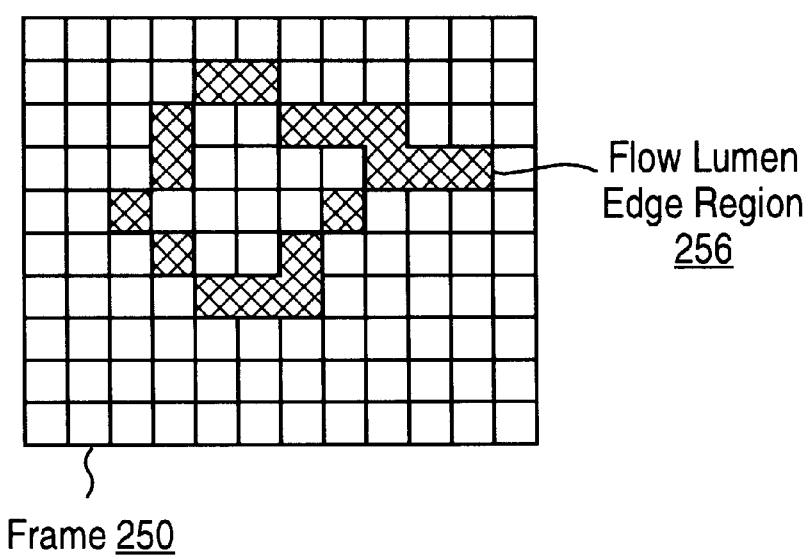
FIGS. 2C is a diagram illustrating determination of the flow lumen edge of a flow structure according to one embodiment of the invention.

It should be appreciated that there are several alternatives to the embodiment described with reference to FIGS. 2A–2C. For example, while FIGS. 2A–2C illustrate determining flow lumen edge pixels for one frame, in alternative embodiments, flow lumen edge determination may be performed for voxels (three-dimensional pixels) or a series of 2D frames (e.g., after generating a three-dimensional image of a flow structure). Furthermore, in an alternative embodiment, volumetric samples, intersecting 2D planes, and/or other samples representing regions in a body may be processed to determine a flow lumen edge.

Furthermore, in an alternative embodiment, the flow lumen edge is constructed with non-flow pixels, rather than flow pixels, that are in proximity or adjacent to flow pixels. For example, in one embodiment, the flow lumen edge pixel region is comprised of non-flow pixels that are adjacent to at least one flow pixel. Thus, flow pixels and/or non-flow pixels may be used to construct the flow lumen edge.

Moreover, in an alternative embodiment, flow lumen edge determination may not be performed using flow or non-flow pixels. In one embodiment, a region defined by a threshold difference (e.g., a substantial Doppler amplitude and/or frequency difference) between two regions may be taken as a flow lumen edge. In such an embodiment of the invention, the signals corresponding to the flow lumen edge for samples (e.g., parallel 2-D planes) may be processed to generate a three-dimensional image of the flow lumen. For example, the signals corresponding to the flow lumen edge may be converted to digital display data (e.g., pixels, voxels, etc.) that may be stored and/or utilized to render a three-dimensional image of the flow structure, and in particular, its flow lumen.

Figure 3A:
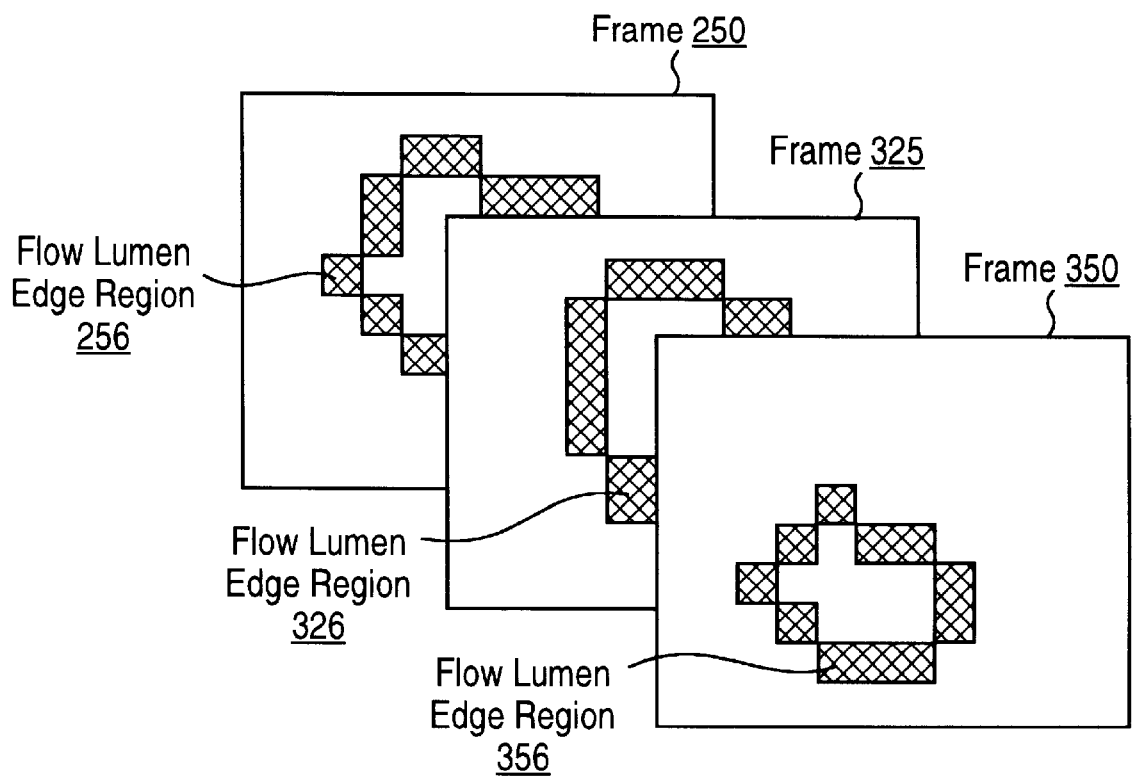
FIG. 3A is a diagram illustrating rendering of a three-dimensional (3D) image of a flow structure, and in particular, its flow lumen, according to one embodiment of the invention.

FIG. 3A is a diagram illustrating rendering of a three-dimensional (3D) image of a flow structure, and in particular, its flow lumen, according to one embodiment of the invention. Shown in FIG. 3A is the frame 250 including the flow lumen edge region 256, as was described with reference to FIGS. 2A–2C. FIG. 3A also depicts a frame 325 and a frame 350, which include a flow lumen edge region 326 and a flow lumen edge region 356, respectively. The frames 325 and 350 may represent, for example, data obtained for 2D planes that are parallel to the frame 250. However, in alternative embodiments, the frames 325 and 350 may represent planes that intersect the plane defined by the frame 250, as described below with reference to FIGS. 3B–3C.

The flow lumen edge regions 326 and 356 may represent portions, at various other planes/slices, of the flow structure represented by the flow region 252 of FIG. 2B. The various planes, in one embodiment, are substantially parallel to each other. By obtaining data for a series of such substantially parallel frames (e.g., by repeating steps 104 and 106), a volumetric 3D image of a flow structure, and in particular, its flow lumen may be constructed.

Figure 3B:
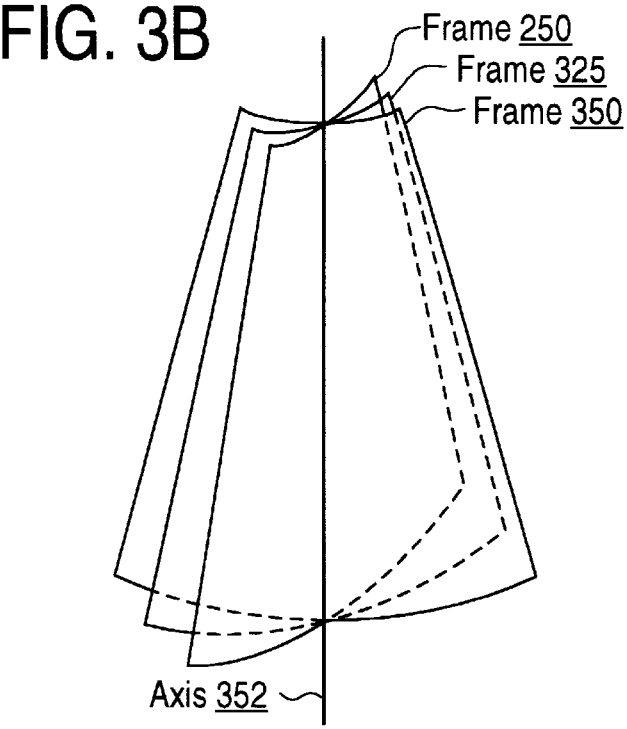
FIG. 3B is a diagram illustrating axially-intersecting 2D imaging planes utilized to generate a volumetric 3D data set according to one embodiment of the invention.

FIG. 3B is a diagram illustrating axially-intersecting 2D imaging planes utilized to generate a volumetric 3D data set according to one embodiment of the invention. Shown in FIG. 3B is the frame 250, as was described with reference to FIGS. 2A–2C, and FIG. 3A. FIG. 3B also depicts the frame 325 and a frame 350, also described with reference to FIG. 3A. The frames 325 and 350 may represent, for example, data obtained for 2D planes that intersect the frame 250 through an axis 352. By obtaining data for a series of such intersecting frames (e.g., by repeating steps 104 and 106), a volumetric 3D image of a flow structure, and in particular, its flow lumen may be constructed.

Figure 3C:
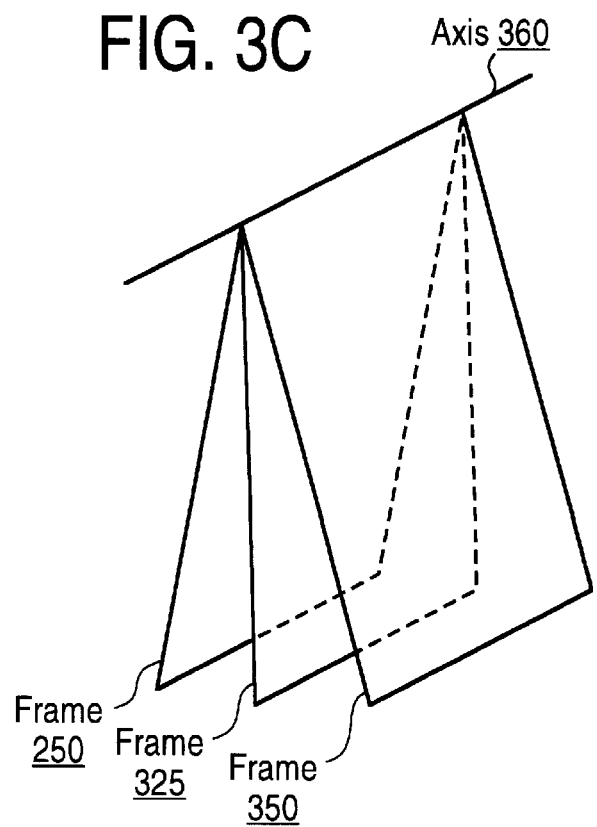
FIG. 3C is a diagram illustrating laterally-intersecting 2D imaging planes utilized to generate a volumetric 3D data set according to one embodiment of the invention.

FIG. 3C is a diagram illustrating laterally-intersecting 2D imaging planes utilized to generate a volumetric 3D data set according to one embodiment of the invention. Shown in FIG. 3C is the frame 250, as was described with reference to FIGS. 2A–2C, and FIG. 3A–3B. FIG. 3C also depicts the frame 325 and a frame 350, also described with reference to FIGS. 3A–3B. The frames 325 and 350 may represent, for example, data obtained for 2D planes that meet the frame 250 at an axis 360. By obtaining data for a series of such frames that meet at an axis (e.g., by repeating steps 104 and 106), a volumetric 3D image of a flow structure, and in particular, its flow lumen may be constructed.

Rendering of a 3D display image of a flow structure, and in particular, its flow lumen, based on 2D samples may be achieved according to several techniques. For example, FIG. 4 depicts two exemplary techniques for 3D display image rendering.

Figure 4:
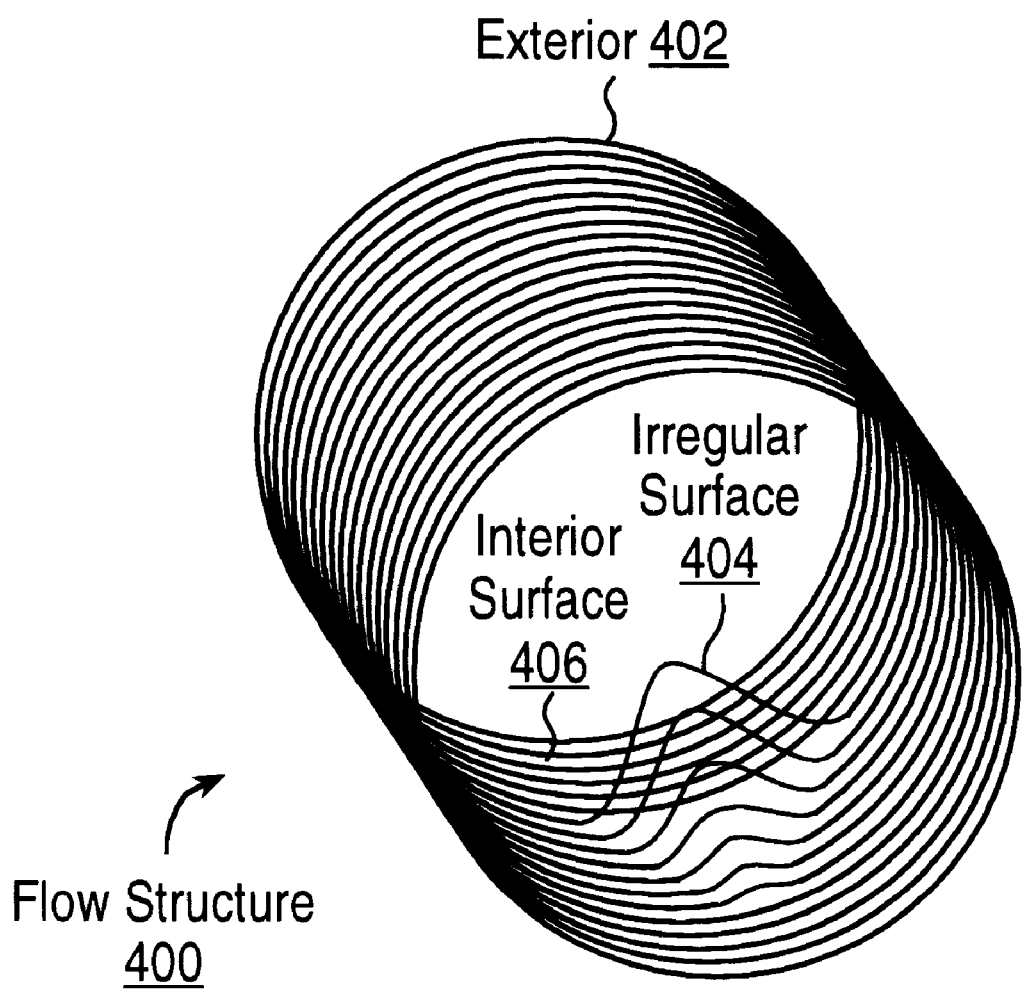
FIG. 4 illustrates an exemplary three-dimensional (3D) image of a flow structure, and in particular, its flow lumen as may be viewed from one end looking into its interior surface, as generated for display using a "wire frame" flow lumen edge rendering method according to one embodiment of the invention.

FIG. 4 illustrates an exemplary three-dimensional (3D) image of a flow structure, and in particular, its flow lumen as may be viewed from one end looking into its interior surface, as generated for display using a "wire frame" flow lumen edge rendering method according to one embodiment of the invention. As shown, the 3D image of a flow structure 400 is generated using wire frame 3D rendering of a series of 2D flow lumen edge pixels, as described, for example, according to the description of FIGS. 3A–3C. That is, a number of parallel and/or intersecting planes of data representing flow regions, non-flow regions, and/or a flow lumen edge region may be "built up" to generate a volumetric three-dimensional image.

The three-dimensional flow structure 400 is shown having an exterior surface 402 and an interior surface 406 which define the flow lumen. As depicted in FIG. 4, the interior surface 406 has an irregular surface 404. For example, the flow structure 400 may represent an artery, vein, or other vessel, and the irregular surface 404 may represent plaque, an intimal defect, etc., in the artery. By providing a three-dimensional image of the flow lumen, and in particular, the flow lumen edge of a flow structure, rather than a solid representation as provided by past ultrasound imaging techniques, such irregular surfaces and other characteristics of the flow lumen, and in particular, the flow lumen edge, may be represented.

The interior surface 406 may approximate, in many cases, the inner physical wall of a flow structure, depending on the Doppler thresholds, pixel resolution, etc. However, this may not necessarily be the case. For example, the physical wall of a flow structure (e.g., the physical interior wall of the lumen of an artery) does not provide flow, and may thus be regarded as a non-flow region to ultrasound (e.g., Doppler) imaging equipment. Additionally, in some instances, there may be a region of non-flow between the actual physical wall of a flow structure and the flow lumen edge as determined using one or more of the ultrasound techniques of the present invention.

One technique for displaying a three dimensional image of a flow structure and/or its flow lumen—namely, wireframe 3D rendering—has been described, alternative embodiments may use other techniques for displaying the flow lumen of a flow structure in 3D, such as opaque rendering, wherein an opaque "sheath" defines the displayed image of a flow structure and its flow lumen. In one embodiment, a user may be able to select between wire frame, opaque, and/or other rendering techniques for displaying a three-dimensional image of a flow structure and/or its flow lumen.

In one embodiment, 3D images of a flow structure may be displayed in color, and further, the images may be "color mapped," so as to provide contrast, depth perspective, etc. In one embodiment, 3D images of flow structures may are color mapped such that relatively near/close regions are depicted by one or more relatively bright colors/shades, while relatively distant regions are depicted by one or more relatively dark colors/shades.

In alternative embodiments, color mapping according to several techniques (e.g., variation of colors/shades may be used to depict depth perspective or side illumination and shadowing, different brightness may be used to depict depth, thickness, etc.). Furthermore, alternative embodiments of the invention may not produce/display images in color and/or color map such displays.

In one embodiment, viewing angles and/or distances of images generated according to the present invention, such as the flow structure 400, may be changed/adjusted under control of a user. For example, using a pointing/stylus device such a trackball, mouse, joystick, etc., the user may be able to adjust an image such as the flow structure 400 in several directions, and even "fly through" the flow lumen. In a virtual angioscopic view, a flow lumen may be displayed to simulate "being and/or moving inside/through" the flow lumen. In one embodiment, various display direction/position/angle/view adjustments may be performed in real-time and provide several directions, angles, and/or positions of view for a flow lumen and/or its flow lumen edge characteristics. Such views may be especially useful in detecting branches, plaque, intimal defects, stenosis, stents, and/or any other irregular regions in arteries, veins, or other vessels.

Figure 5:
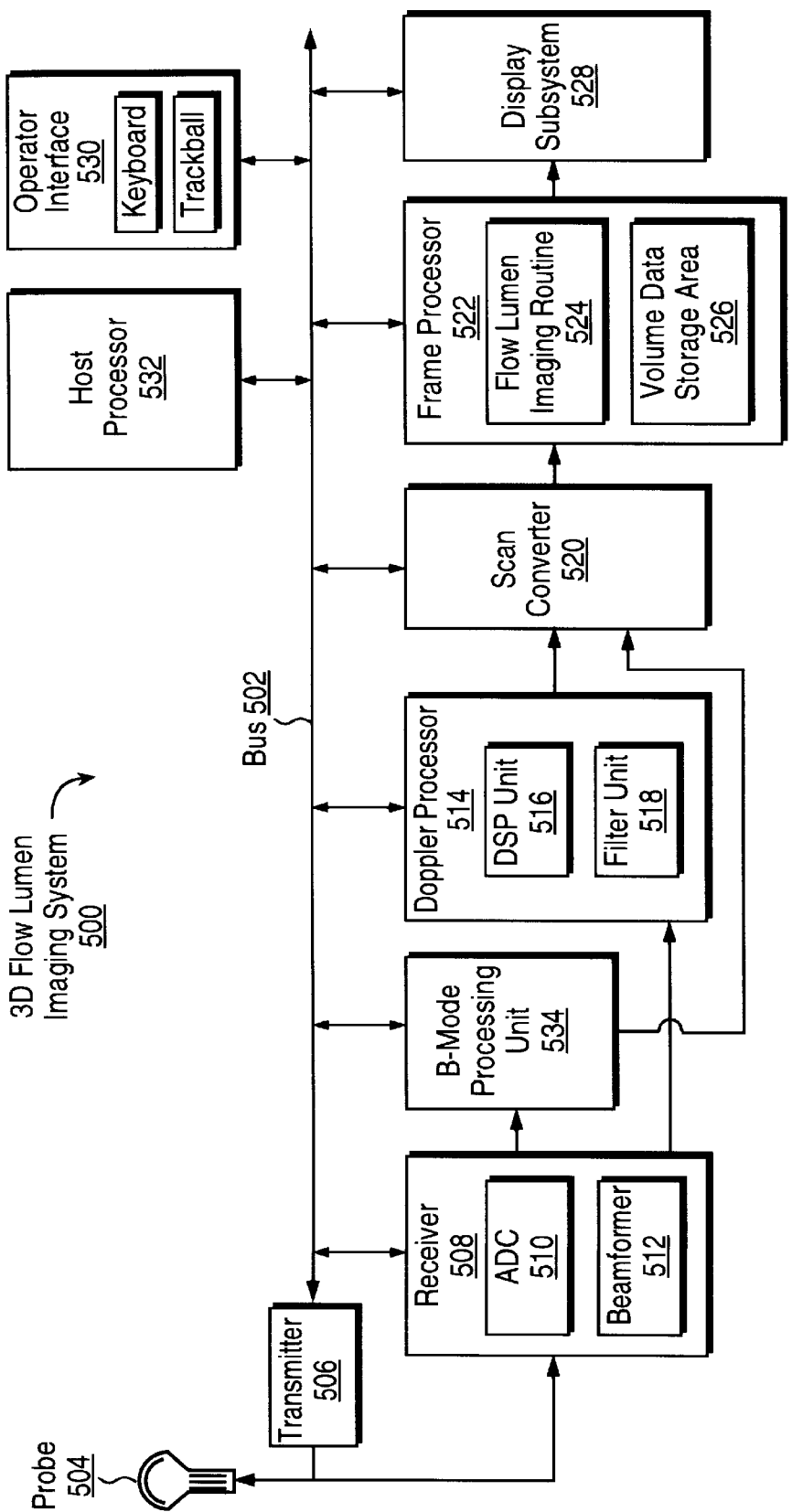
FIG. 5 is a block diagram illustrating an ultrasound imaging system operable to provide three dimensional images of flow structures, and in particular, flow lumen, according to one embodiment of the present invention.

FIG. 5 is a block diagram illustrating an ultrasound imaging system operable to provide three dimensional images of flow structures, and in particular, flow lumen, according to one embodiment of the present invention. An imaging system 500 is shown, which includes a probe 504 coupled to a transmitter 506 and a receiver 508. The receiver 508 is operable to receive and focus reflected signals, from a body, for example, via the probe 504. In one embodiment of the invention, as shown in FIG. 5, the receiver 508 includes an analog-to-digital converter (ADC) unit 510 and a beamformer 512.

The receiver 508 is coupled to provide data to a Doppler processor 514, which includes a digital signal processing (DSP) unit 516 to process digitized Doppler signals and a filter unit 518 to filter the Doppler signals. In one embodiment, the Doppler processor 514 is operable to process color Doppler information (e.g., frequency shift). Thus, 2D color Doppler data may be generated. In an alternative embodiment, the Doppler processor 514 is operable to process power/magnitude Doppler information. In yet another embodiment, the Doppler processor 514 is operable in one or more modes to process a combination of several types of Doppler information (e.g., frequency shift, power/magnitude, etc.).

Additionally, the system 500 includes a B-Mode processing unit 534, coupled between the receiver 508 and the scan converter 520. The B-Mode processing unit 534 may include several types of circuitry, such as a demodulator, filter, etc. In one embodiment, during frame acquisition, Doppler information may be superimposed on B-Mode information. B-Mode information typically provides tissue structure imaging. Thus, in one embodiment of the invention, flow structures and tissue structures, which may be generated with maximum amplitude projection of 3D B-Mode information, may simultaneously and/or selectively be displayed. While one embodiment of the invention that includes B-Mode processing circuitry has been described, it should be appreciated that alternative embodiments of the invention may not include B-Mode processing circuitry.

As shown, the Doppler processor 514 and the B-Mode processing unit 534 are further coupled to a scan converter 520. The scan converter 520 is operable to generate image data based on Doppler and/or B-Mode information. As shown, the scan converter 520 is further coupled to a frame processor 522. While one embodiment is described wherein the B-Mode processing unit 534 and the Doppler processor 514 are coupled to a scan converter, in alternative embodiments, each of the B-Mode processing unit 534 and the Doppler processor 514 may include a dedicated scan converter.

The frame processor 522 includes a flow lumen imaging routine 524 and a volume data storage area 526. The flow lumen imaging routine 524, in one embodiment, includes a number of machine-executable instructions and/or circuitry to provide 3-D images of flow lumen, according to the present invention. The flow lumen imaging routine 524 may be stored on a machine-readable medium (e.g., magnetic disk, optical disk, etc.), in a memory (e.g., a dynamic random access memory (DRAM), static random access memory (SRAM), read-only memory (ROM), etc.), or a combination or data storage devices/media. Similarly, the volume data storage area 526 may be implemented as a machine-readable medium (e.g., magnetic disk, optical disk, etc.), a memory (e.g., DRAM, SRAM, ROM, etc.), or a combination or data storage devices/media.

It should be appreciated that the frame processor 522 may include a number of frame processing routines and/or circuitry not shown in FIG. 5. For example, in one embodiment, the frame processor 522 may include a temporal filtering routine, a frame compounding unit, a color display mapping routine, etc. Furthermore, one or more of the routines may be stored in devices other than the frame processor 522 in the system 500. It should further be appreciated that several combinations of software routines and/or hard-wired circuitry may be utilized by the frame processor 522 to perform one or more frame processing functions in alternative embodiments of the invention.

As shown, the frame processor 522 is further coupled to a display subsystem 528. The display subsystem 528 comprises one or more display devices to provide viewing of images (e.g., of flow lumen) generated according to the present invention.

The transmitter 506, the receiver 508, the Doppler processor 514, the Doppler scan converter 520, the frame processor 522, and the display subsystem are shown coupled to a bus 502. In one embodiment, the bus 502 provides transfer of control signals from a host processor 532 shown coupled to the bus 502.

Also shown coupled to the bus 502 is an operator interface 530, which, in one embodiment, may include a keyboard and a trackball. In alternative embodiments, the operator interface 530 may include one or more other types of user input devices (e.g., a trackpad, a mouse, a joystick, etc.). In one embodiment, the operator interface 530 provides control of viewing parameters/options (e.g., viewing angles/directions/positions/distances, virtual angioscopic viewing, wire-frame vs. opaque and/or other 3D rendering, color mapping options, etc.) of 3D images of flow structures and/or flow lumen that may be generated by the system 500.

It should be understood that the system 500 may include several other devices not described herein, and thus, may be implemented as a subsystem in an ultrasound system. Furthermore, it should be understood that while an exemplary ultrasound imaging system has been described according to an embodiment of the invention, alternative embodiments of the invention may utilize several types and combinations of hard-wired devices and/or software instructions to render three-dimensional images of flow lumen using ultrasound data according to the present invention.

ALTERNATIVE EMBODIMENTS

While the invention has been described in terms of several embodiments, those skilled in the art will recognize that the invention is not limited to the embodiments described. In particular, the invention can be practiced in several alternative embodiments to provide three-dimensional images of flow structures, and in particular, of flow lumen based on ultrasound data.

Therefore, it should be understood that the method and apparatus of the invention can be practiced with modification and alteration within the spirit and scope of the appended claims. The description is thus to be regarded as illustrative instead of limiting on the invention.

What is claimed is:

1. A method for generating an ultrasound-based image of a flow lumen, said method comprising:
   based on a set of Doppler signals, determining that a first set of pixels represents an area of flow;
   based on said set of Doppler signals, determining that a second set of pixels represents an area of non-flow;
   isolating edge pixels substantially representing a border between said area of flow and said area of non-flow; and
   deriving said image from said edge pixels.

2. The method of claim 1, further comprising:
   isolating said edge pixels for a plurality of two-dimensional planes; and
   generating said image as a three-dimensional (3D) image of said edge pixels for said plurality of two-dimensional planes.

3. The method of claim 2, further comprising:
   displaying said image.

4. The method of claim 3, further comprising:
   generating a virtual angioscopic view of the flow lumen.

5. The method of claim 3, further comprising:
   displaying said image using a wire frame three-dimensional rendering of the flow lumen.

6. The method of claim 3, further comprising:
   displaying the image using an opaque frame three-dimensional rendering of the flow lumen of the flow structure.

7. The method of claim 3, further comprising:
   displaying said image in color.

8. The method of claim 7, further comprising:
   mapping said image according to color brightness to provide depth perspective.

9. The method of claim 7, further comprising:
   mapping said image according to color brightness to provide side illumination and shadowing.

10. The method of claim 1, wherein the Doppler signals provide power Doppler information to detect said areas of flow and non-flow.

11. The method of claim 1, wherein the Doppler signals provide frequency shift Doppler information.

12. An apparatus for use in a Doppler-based ultrasound imaging system, said apparatus comprising:
    a probe to exchange Doppler signals with a body;
    a processing unit, coupled to said probe, to identify, based on flow information provided by said Doppler signals, a region of flow and a region of non-flow, and to determine a boundary therebetween to generate image data of a flow lumen derived from said boundary between said area of flow and said area of non-flow.

13. The apparatus of claim 12, further comprising:
    a display, coupled to said processing circuit, to display an image generated from said image data.

14. The apparatus of claim 12, wherein said processing unit comprises:
    a Doppler processing circuit to process ultrasound echo signals from a body used to determine said area of flow and said area of non-flow.

15. The apparatus of claim 12, wherein said Doppler signals are associated with power Doppler data.

16. The apparatus of claim 12, wherein said Doppler signals are associated with frequency shift Doppler data.

17. The apparatus of claim 13, further comprising:
    an input device, coupled to said processing unit, to control viewing characteristics of said image.

18. The apparatus of claim 17, wherein said display provides an interactively-controllable view of said flow lumen.

19. A method for generating an image of a flow lumen, said method comprising:
    receiving a first set of Doppler echo signals from a body;
    determining that said first set of Doppler echo signals indicate a region of non-flow;
    receiving a second set of Doppler echo signals from a body;
    determining that said second set of Doppler echo signals indicate a region of flow;

mapping said first and second regions into a plurality of pixels, wherein pixels of a first type correspond to said region of flow and pixels of a second type correspond to said region of non-flow;

isolating a set of pixels from said plurality of pixels, wherein said set of pixels represents an edge between said first and second types of pixels; and generating said image from said set of pixels.

20. The method of claim 19, further comprising:

isolating said set of pixels by identifying pixels that are surrounded by at least one pixel of said first type and one pixel of said second type.

21. The method of claim 19, further comprising:

displaying said image, which represents said flow lumen.

22. The method of claim 21, further comprising:

generating a virtual angioscopic view of said flow lumen.

23. The method of claim 19, wherein said Doppler echo signals provide power Doppler information to determine said regions of flow and non-flow.

24. The method of claim 19, wherein said Doppler echo signals provide frequency shift Doppler information.

* * * * *